(12) United States Patent
Nanaumi

(10) Patent No.: US 9,566,006 B2
(45) Date of Patent: Feb. 14, 2017

(54) OBJECT INFORMATION ACQUISITION APPARATUS

(71) Applicant: CANON KABUSHIKI KAISHA, Tokyo (JP)

(72) Inventor: Ryuichi Nanaumi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 517 days.

(21) Appl. No.: 14/073,184

(22) Filed: Nov. 6, 2013

(65) Prior Publication Data

US 2014/0135610 A1     May 15, 2014

(30) Foreign Application Priority Data

Nov. 15, 2012   (JP) .................................. 2012-251317

(51) Int. Cl.
    *A61B 5/05*        (2006.01)
    *A61B 5/00*        (2006.01)
    *A61B 5/145*      (2006.01)

(52) U.S. Cl.
    CPC ......... *A61B 5/0095* (2013.01); *A61B 5/14542* (2013.01); *A61B 5/4312* (2013.01)

(58) Field of Classification Search
None
See application file for complete search history.

(56) References Cited

U.S. PATENT DOCUMENTS

| | | | |
|---|---|---|---|
| 8,144,327 B2 | 3/2012 | Nakajima et al. | 356/432 |
| 2009/0002685 A1* | 1/2009 | Fukutani et al. | 356/72 |
| 2010/0070233 A1* | 3/2010 | Masumura | 702/127 |
| 2010/0191109 A1* | 7/2010 | Fukutani et al. | 600/437 |
| 2011/0172513 A1* | 7/2011 | Nakajima et al. | 600/407 |
| 2011/0245652 A1 | 10/2011 | Oishi | 600/407 |
| 2011/0261056 A1 | 10/2011 | Fukutani | 345/440 |
| 2012/0123256 A1* | 5/2012 | Razansky et al. | 600/431 |

(Continued)

FOREIGN PATENT DOCUMENTS

| | | |
|---|---|---|
| EP | 2345364 | 7/2011 |
| JP | 2011-245277 | 12/2011 |

(Continued)

OTHER PUBLICATIONS

Extended European Search Report issued Dec. 27, 2013 in counterpart European Patent Application No. 13190007.8.

(Continued)

*Primary Examiner* — James Kish
(74) *Attorney, Agent, or Firm* — Fitzpatrick, Cella, Harper & Scinto

(57) ABSTRACT

An object information acquisition apparatus comprises an irradiating unit configured to irradiate an object with light; a plurality of detecting units configured to receive an elastic wave generated within the object irradiated with light, and convert the elastic wave to a received signal; a distribution acquiring unit configured to acquire a light intensity distribution within the object irradiated with light; a setting unit configured to select a minimum block unit in which light intensity is greater than or equal to a predetermined threshold value, using the light intensity distribution; and a generating unit configured to generate object information of the minimum block unit selected by the setting unit, using the received signal.

20 Claims, 12 Drawing Sheets

(56) References Cited

U.S. PATENT DOCUMENTS

| | | | |
|---|---|---|---|
| 2012/0289812 A1 | 11/2012 | Oishi | 600/407 |
| 2013/0160558 A1 | 6/2013 | Oishi | 73/655 |
| 2013/0253322 A1 | 9/2013 | Suzuki et al. | 600/443 |
| 2013/0335441 A1* | 12/2013 | Zalev | A61B 5/7203 345/629 |

FOREIGN PATENT DOCUMENTS

| | | |
|---|---|---|
| JP | 2012-061055 | 3/2012 |
| JP | 2012-085965 | 5/2012 |
| WO | WO 2011/096551 A | 8/2011 |
| WO | WO 2011/125468 A | 10/2011 |
| WO | WO 2012/086842 A | 6/2012 |
| WO | WO 2012/144395 A | 10/2012 |

OTHER PUBLICATIONS

Chinese (P.R. China) Office Action issued Apr. 3, 2015 in counterpart Chinese Patent Application No. 201310562373.3, with translation.

\* cited by examiner

OBJECT INFORMATION ACQUISITION APPARATUS

BACKGROUND OF THE INVENTION

Field of the Invention

The present invention relates to an object information acquisition apparatus.

Description of the Related Art

As one in vivo imaging technique using near-infrared light, there is photoacoustic tomography (PAT). In PAT, an object such as a biological body is irradiated with pulsed light generated from a light source, whereby light propagated and diffused within the object is absorbed by a light absorber to generate an elastic wave. This mechanism of elastic wave generation is called a photoacoustic effect. Since a tumor has a higher light energy absorption rate for near-infrared light than surrounding tissues, the tumor absorbs more light than the surrounding tissues. Thus, the tumor momentarily expands and generates an elastic wave.

In an apparatus described in Japanese Patent Application Laid-open No. 2011-245277, the elastic wave is detected with a detection element and converted to a received signal. Through signal processing (reconstruction) of the received signal, object information such as the space distribution of initial sound pressure of the elastic wave generated upon absorption of light energy within the object can be imaged. Since the space distribution of generated sound pressure relates to the absorption coefficient of light, diagnosis of an object using space distribution relating to the absorption coefficient of light has been studied.

SUMMARY OF THE INVENTION

The present invention in its one aspect provides an object information acquisition apparatus comprising an irradiating unit configured to irradiate an object with light; a plurality of detecting units configured to receive an elastic wave generated within the object irradiated with light, and convert the elastic wave to a received signal; a distribution acquiring unit configured to acquire a light intensity distribution within the object irradiated with light; a setting unit configured to select a minimum block unit in which light intensity is greater than or equal to a predetermined threshold value, using the light intensity distribution; and a generating unit configured to generate object information of the minimum block unit selected by the setting unit, using the received signal.

Further features of the present invention will become apparent from the following description of exemplary embodiments with reference to the attached drawings.

DESCRIPTION OF THE EMBODIMENTS

Figure 1:
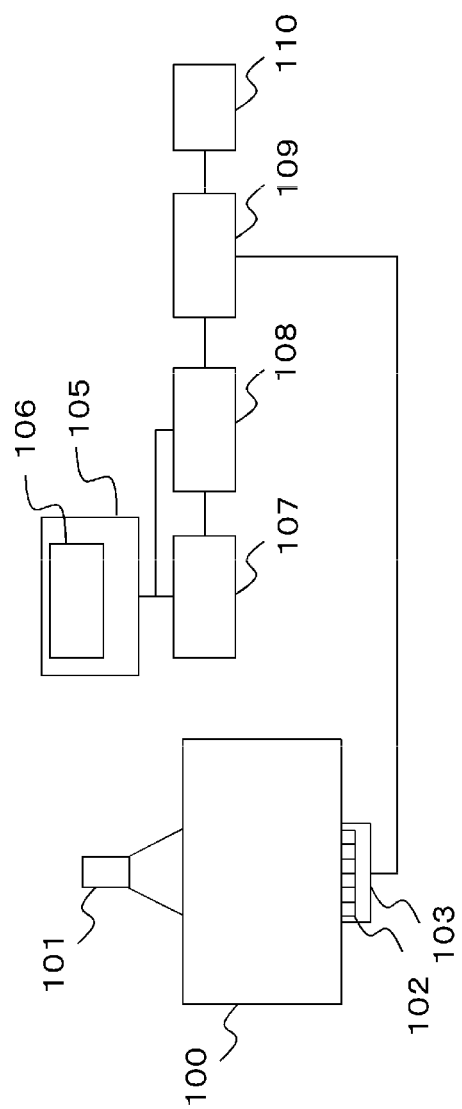
FIG. 1 is a diagram showing an overview of a photoacoustic imaging apparatus in a first embodiment.

A preferred embodiment of the present invention will be described below with reference to the drawings. Note that the dimension, material, and shape of components, the relative arrangement thereof, and the like described below should be changed appropriately depending on the configuration of an apparatus or various conditions to which the invention is applied and are not intended to limit the scope of this invention to the description below.

In the present invention, an acoustic wave includes an elastic wave called a sound wave, ultrasound wave, photoacoustic wave, or light-induced ultrasound wave. An object information acquisition apparatus of the present invention is an apparatus utilizing a photoacoustic effect in which an acoustic wave generated within an object by irradiating the object with light (electromagnetic wave) is received and characteristic information within the object is acquired.

Object information in the object information acquisition apparatus is the characteristic information reflecting the initial sound pressure of an acoustic wave caused by light irradiation, light energy absorption density derived from the initial sound pressure, absorption coefficient, concentration of a substance forming a tissue, or the like. The concentration of a substance is, for example, the concentration of oxygenated hemoglobin and reduced hemoglobin or oxygen saturation. The characteristic information may be distribution information of each position within an object instead of numerical data. That is, initial sound pressure distribution, absorption coefficient distribution, oxygen saturation distribution, or the like may be generated into image data.

The present invention can be understood as a control method upon receiving an acoustic wave with the object information acquisition apparatus. In the embodiments below, a photoacoustic imaging apparatus will be described as a specific example of the object information acquisition apparatus. In the respective drawings, the same components are basically denoted by the same reference numerals, and descriptions will be omitted.

First Embodiment

First, the relationship of sound pressure of an elastic wave caused by a photoacoustic effect and light intensity within an object will be described. A sound pressure $p_0$ (Pa) of the elastic wave caused by the photoacoustic effect is represented by Formula (1).

[Math. 1]

$$p_0 = \mu_a \cdot \Gamma \cdot \Phi \tag{1}$$

In Formula (1), $\mu_a$ is the absorption coefficient ($mm^{-1}$) of a light absorber (tumor or the like), $\Gamma$ is the Gruneisen coefficient, and $\Phi$ is the light intensity ($J/mm^2$) at a position of the light absorber. The Gruneisen coefficient Γ is a value for which a value of the volume expansion coefficient multiplied by the square of the speed of sound is divided by the constant pressure specific heat, and takes an approximately constant value in vivo.

As can be seen from Formula (1), the generated sound pressure is proportional to light intensity. In the case where a strong light scatterer such as a biological body is the object, the light intensity Φ decays exponentially in accordance with the distance from the position irradiated with light. Therefore, the light intensity decreases due to decay, and a domain where an elastic wave with sufficient sound pressure to be detected is not generated exists. Since it is difficult to acquire the object information with high precision even if reconstruction is performed with respect to such a domain where the light intensity is low, the inventor of the present invention has found that the significance of performing the reconstruction is small.

In a first embodiment, an optical characteristic value of the object is input to an apparatus, and a domain for which the object information is acquired is limited based on the light intensity distribution calculated from the optical characteristic value to shorten the time required for acquisition of the object information. As the optical characteristic value, the absorption coefficient that is an absorption characteristic value and the reduced scattering coefficient that is a scattering characteristic value are used.

(Apparatus Configuration)

FIG. 1 is a diagram showing an overview of a photoacoustic imaging apparatus in this embodiment. The configuration for acquiring information of an object will be described below.

A light source of the present invention includes at least one coherent or incoherent pulsed light source. In order to generate a photoacoustic effect, the pulse width is preferably several hundred nanoseconds or less. In the case of measurement of a breast cancer or the like, light of a specific wavelength that is absorbed by a specific constituent (for example, hemoglobin) out of constituents forming a biological body is generated. Laser with which a large output can be obtained is preferable as the light source, but it is also possible to use a light-emitting diode or the like instead of the laser. As the laser, various lasers such as solid-state laser, gas laser, dye laser, or semiconductor laser may be used.

An irradiation unit 101 that is irradiating unit irradiates an object 100 with irradiation light from the light source with a method suitable for photoacoustic measurement. In order to increase the SN ratio of a received signal, not only a part of surfaces but also a plurality of surfaces of the object may be irradiated with light. For example, the irradiation unit 101 may be provided not only on the side opposing a probe 103 with respect to the object but also on the same side. The irradiation unit 101 includes a mirror, a lens that collects, magnifies, or changes the shape of light, a prism that disperses, refracts, or reflects light, or an optical fiber. Any such optical part aside from those mentioned above may also be used as long as an object can be irradiated with light emitted from a light source with a desired method (irradiation direction, shape, or the like).

With a transducer 102 that is detecting unit, an elastic wave generated by the object 100 being irradiated with light is received and converted to an electrical signal that is the received signal. The transducer 102 is configured of a transducer using a piezoelectric phenomenon, a transducer using optical resonance, a transducer using capacity change, or the like. Any transducer with which an elastic wave can be received and converted to an electrical signal may be used. In this embodiment, a plurality of the transducers 102 are present in order to receive elastic waves in different positions. The plurality of transducers 102 are, for example, arranged one-dimensionally or two-dimensionally to form the probe 103. The probe 103 outputs the electrical signal generated by the plurality of transducers 102 to a reconstruction unit 109.

An optical characteristic value input unit 106 that is characteristic input unit includes an interface that accepts an input of the optical characteristic value (absorption coefficient and reduced scattering coefficient) of the object 100 performed by an operator. For example, in the case where the object 100 is a biological body, a general value for a biological body may be input or a known statistical value according to a characteristic, e.g., age, of the object 100 may be input as the absorption coefficient and the reduced scattering coefficient. Alternatively, it may be such that, when an input of age or sex is received, a value according thereto is set automatically.

An optical characteristic value setting unit 105 that is characteristic setting unit sets the absorption coefficient and the reduced scattering coefficient input to the optical characteristic value input unit 106 in a light intensity distribution calculation unit 107.

The light intensity distribution calculation unit 107 uses the absorption coefficient and the equivalent scattering coefficient set by the optical characteristic value setting unit 105 to calculate the light intensity distribution inside the object 100. The light intensity distribution calculation unit is distribution acquiring unit of the present invention. As a calculation method for the light intensity distribution, a numerical solution method of transport equations, a numerical solution method of diffusion approximation equations, a numerical solution method using a Monte Carlo method, or the like may be used. It is desirable that an intensity distribution pattern of irradiation light be reflected in the calculation of the light intensity distribution. Accordingly, the precision of calculation of the light intensity distribution can be improved. For example, it is recommended that the irradiation unit 101 be able to monitor the intensity distribution pattern of irradiation light and that the intensity distribution pattern be input to the light intensity distribution calculation unit.

With a light intensity domain setting unit 108 that is setting unit, a minimum block unit within a light intensity domain that is a domain having a light intensity of a predetermined threshold value or greater is extracted and set in the reconstruction unit 109. As the threshold value of light intensity, light intensity with which a minimum sound pressure detectable by the transducer 102 is generated can be utilized, for example.

The predetermined threshold value may differ for each minimum block unit. A calculation method therefor will be described below.

Formula (2) represents a decay compensation noise equivalent sound pressure value $p_{NEP\_c}(r)$ described later. A threshold value $\Phi_{th}(r)$ of light intensity of the minimum block unit of a position vector r is represented by Formula (3) that is a deformation of Formula (1).

[Math. 2]

$$p_{NEP\_c}(r) = \frac{p_{NEP}}{A\left(\alpha, \max_i(|d_i - r|)\right)} \quad (2)$$

-continued

[Math. 3]

$$\Phi_{th}(r) = \frac{p_{NEP\_c}(r)}{\mu_{a\_BG}} \cdot \Gamma \quad (3)$$

In Formula (2), $p_{NEP}$ is the noise equivalent sound pressure for which the intensity of noise included in the electrical signal that is the received signal is divided by the conversion efficiency in the conversion of the sound pressure to the electrical signal by the transducer 102. The unit for the conversion efficiency is V/Pa in the case where the electrical signal is a voltage. In Formula (2), $A(\alpha, \max(|d_i-r|))$ is the decay ratio of sound pressure upon propagation of an elastic wave between the transducer 102 of a position vector $d_i$ (where i is a number showing each of the plurality of transducers 102) and the minimum block unit. The decay coefficient (mm$^{-1}$) of the object 100 and max$|d_i-r|$ that is the greatest among distances $|d_i-r|$ of the i-th transducer 102 and the minimum block unit determine A. The decay of sound pressure includes distance-dependent decay by a decay coefficient $\alpha$ and distance-dependent decay due to energy dissipation in spherical wave propagation, cylindrical wave propagation, or the like.

The noise equivalent sound pressure $p_{NEP}$ is divided and corrected by the decay ratio A for $p_{NEP\_c}(r)$ that is the decay compensation noise equivalent sound pressure value. That is, if the minimum block unit of the position vector r has generated an elastic wave of a sound pressure of $p_{NEP\_c}(r)$, the elastic wave is detected by the transducer 102. Thus, through correction using the decay ratio in the greatest distance max$|d_i-r|$ in which the sound pressure decays most, it can be guaranteed that a transducer in a distance nearer than max$|d_i-r|$ can detect the elastic wave.

The absorption coefficient of the object 100 set in the light intensity distribution calculation unit 107 by the optical characteristic value setting unit 105 is $\mu_{a\_BG}$. The absorption coefficient of tumor presumably has a value greater with respect to $\mu_{a\_BG}$ that is an average coefficient of the object 100. This is because a tumor is rich in blood of a large absorption coefficient since new blood vessels are drawn in. From Formula (1), the sound pressure of the generated elastic wave is small when the absorption coefficient is small. Therefore, at least when $\Phi_{th}(r)$ obtained using $\mu_{a\_BG}$ is the threshold value, an elastic wave caused by the tumor that is a target for imaging can be detected. In Formula (3), $\Gamma$ is the Gruneisen coefficient, and it is recommended that a value typical for a biological body be input in the case where the object 100 is a biological body, for example.

The light intensity domain setting unit 108 calculates the threshold value of light intensity for each minimum block unit in a manner described above.

Figure 2:
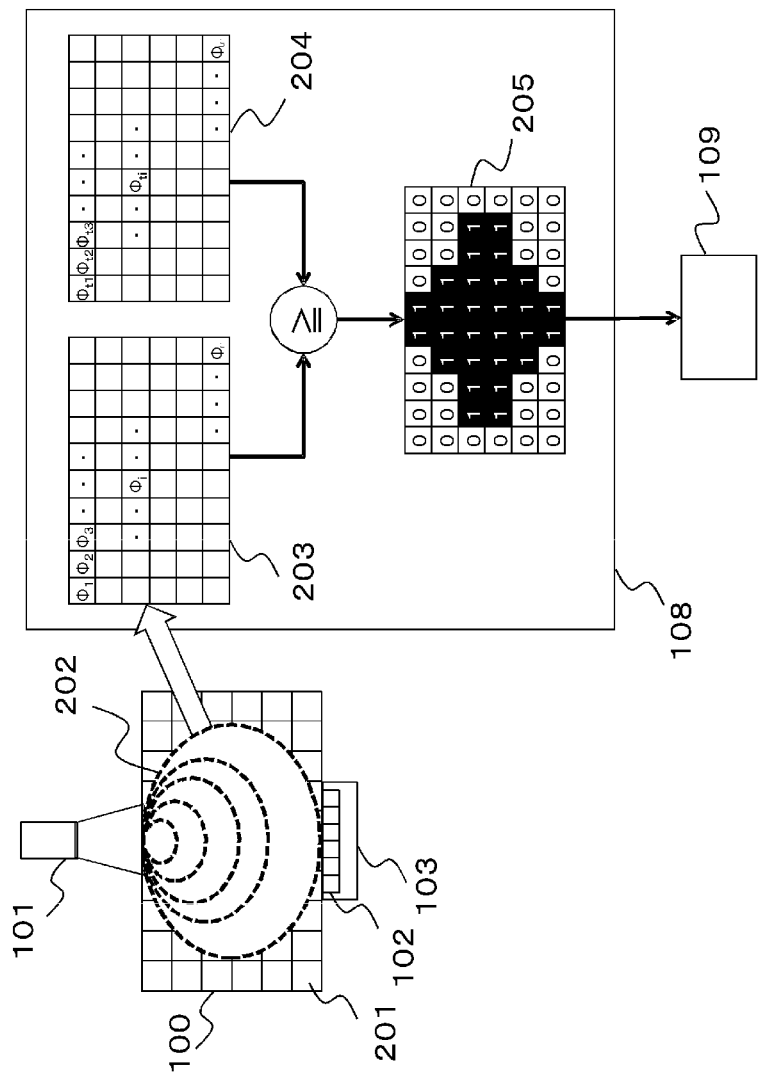
FIG. 2 is a diagram showing the details of a light intensity domain setting unit in the first embodiment.

Next, the light intensity domain will be described. FIG. 2 is a diagram showing the details of the light intensity domain setting unit 108. Reference numeral 202 in the upper left in the drawing shows the light intensity distribution calculated by the light intensity distribution calculation unit 107. The intensity of the light is stronger when nearer the irradiation unit 101. The light intensity distribution 202 is output to the light intensity domain setting unit 108 as a light intensity distribution 203 for each minimum block unit 201.

In the light intensity domain setting unit 108 on the right side in the drawing, $\Phi_i$ shown in the light intensity distribution 203 for each minimum block unit shows the light intensity of the minimum block unit of the number i. When the position vector of the i-th minimum block unit is $r_i$, $\Phi_i = \Phi(r_i)$ (where $\Phi(r_i)$ is the light intensity of the minimum block unit of the position vector $r_i$). Reference numeral 204 denotes a threshold value of light intensity for each minimum block unit that is calculated for each minimum block unit by Formula (2) and Formula (3). The threshold value of light intensity of the minimum block unit of the number i is shown by $\Phi_{ti}$ shown in the threshold value 204 of light intensity for each minimum block unit. In a similar manner to reference numeral 203, $\Phi_{ti} = \Phi_{th}(r_i)$.

The light intensity domain setting unit 108 further includes a light intensity domain storage unit 205 that stores a value corresponding to each minimum block unit forming the object 100. The light intensity domain setting unit 108 compares $\Phi_i$ and $\Phi_{ti}$ of the same number i, and sets 1 in a storage area for the corresponding minimum block unit in the light intensity domain storage unit 205 if $\Phi_i \geq \Phi_{ti}$. The light intensity domain setting unit 108 sets 0 in a storage area other than for the corresponding minimum block unit. A domain of black minimum block units shown in the light intensity domain storage unit 205 is a light intensity domain. The light intensity domain setting unit 108 sets the minimum block unit within the light intensity domain in the reconstruction unit 109 by outputting a value in the light intensity domain storage unit 205 to the reconstruction unit 109.

The reconstruction unit 109 as generating unit generates (reconstructs) photoacoustic image data using a plurality of the electrical signals output from the probe 103. As a method of reconstruction, a back projection method or the like with time domain or Fourier domain that is normally used in a tomography technique may be used. The photoacoustic image data in the present invention, whether in two dimension or three dimension, refers to data showing information (biological information such as in vivo initial sound pressure distribution, light absorption coefficient distribution, or oxygen saturation) inside the object. The photoacoustic image data is configured as an arrangement of a plurality of pixels that are the minimum block units in a two-dimensional case, and is configured as an arrangement of a plurality of voxels that are the minimum block units in a three-dimensional case.

The reconstruction unit 109 selectively reconstructs the minimum block unit within the light intensity domain set by the light intensity domain setting unit 108 that is the setting unit out of the minimum block units forming the object 100, and generates data with which the inside of the object 100 is imaged.

The data with which the inside of the object 100 is imaged is transferred to a display unit 110 and displayed with respect to the operator.

The light intensity distribution calculation unit 107, the light intensity domain setting unit 108, and the reconstruction unit 109 described above may be a program installed in a computer or may be an electronic circuit.

Figure 3:
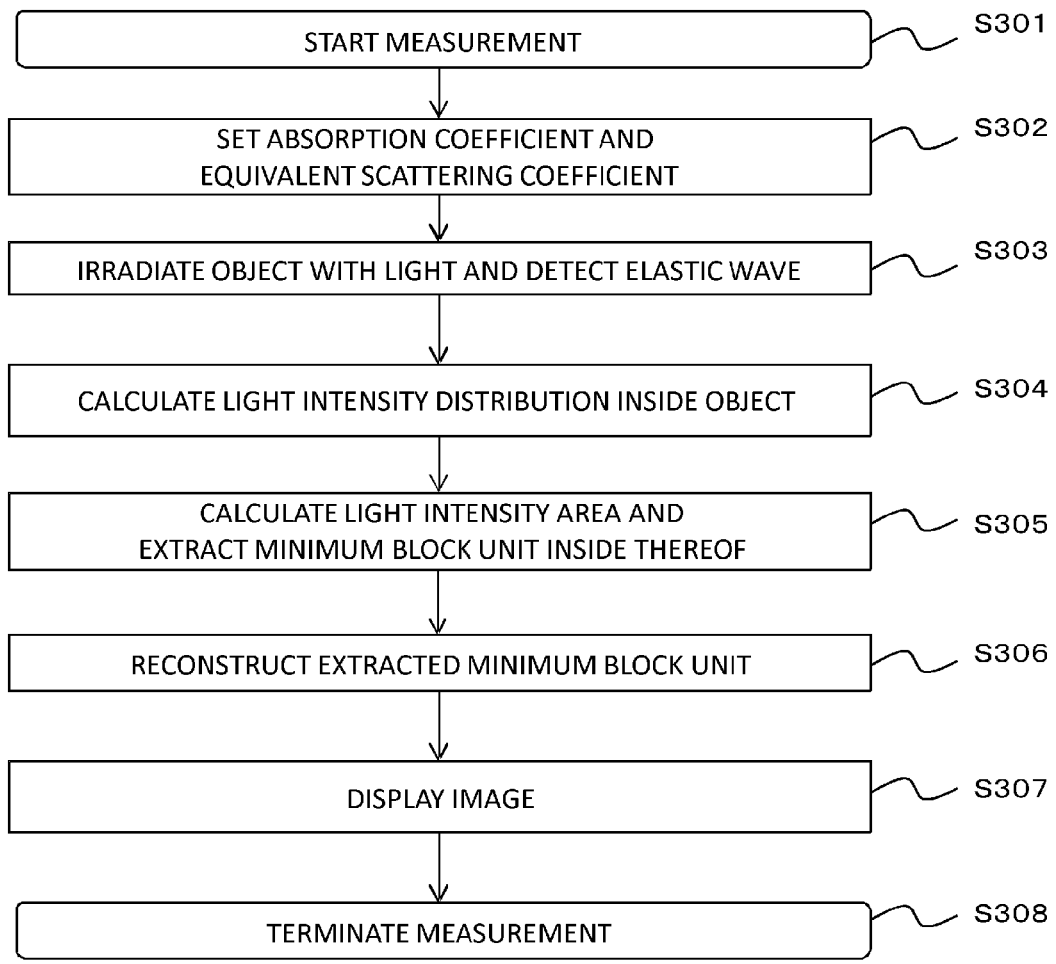
FIG. 3 is a diagram showing the flow of measurement in the first embodiment.

The flow of measurement in this embodiment is shown in FIG. 3.

In step S301, the measurement is started.

In step S302 that is a characteristic setting step, the operator executes a characteristic inputting step of inputting the optical characteristic value (the absorption coefficient and the equivalent scattering coefficient) of the object 100 from the optical characteristic value input unit 106. The input absorption coefficient and equivalent scattering coefficient are set in the light intensity distribution calculation unit 107 and the light intensity domain setting unit 108.

In step S303 that is a detecting step, the object 100 irradiated with light from the irradiation unit 101, and the elastic wave generated in the object 100 by light irradiation is detected by the transducer 102. The detected elastic wave is output as the received signal from the probe 103.

In step S304 that is a distribution acquiring step, the light intensity distribution inside the object 100 is calculated in the light intensity distribution calculation unit 107 using the absorption coefficient and the equivalent scattering coefficient input in step S302.

In step S305 that is a setting step, the light intensity domain is calculated and the minimum block unit inside the light intensity domain is extracted by the light intensity domain setting unit 108 using the absorption coefficient input in step S302 and the light intensity distribution obtained in step S304. The extracted minimum block unit is set in the reconstruction unit 109.

In step S306 that is a generating step, the minimum block unit extracted and set in step S305 is reconstructed in the reconstruction unit 109 using the received signal obtained in step S303. Accordingly, image data of the inside of the object is obtained.

In step S307, the image data of the inside of the object obtained in step S306 is displayed in the display unit 110.

In step S308, the measurement is terminated.

In the first embodiment, the minimum block units to be reconstructed can be reduced and the time until acquisition of the object information can be shortened by selectively reconstructing the minimum block unit included in a domain having sufficient light intensity obtained from the input optical characteristic value of the object.

Second Embodiment

In a second embodiment, an optical characteristic value of an object is actually measured and acquired, and a domain for which object information is acquired is limited based on the light intensity distribution calculated from the optical characteristic value to shorten the time required for the acquisition of the object information. As the optical characteristic value, the absorption coefficient that is an absorption characteristic value and the equivalent scattering coefficient that is a scattering characteristic value are measured.

(Apparatus Configuration)

Figure 4:
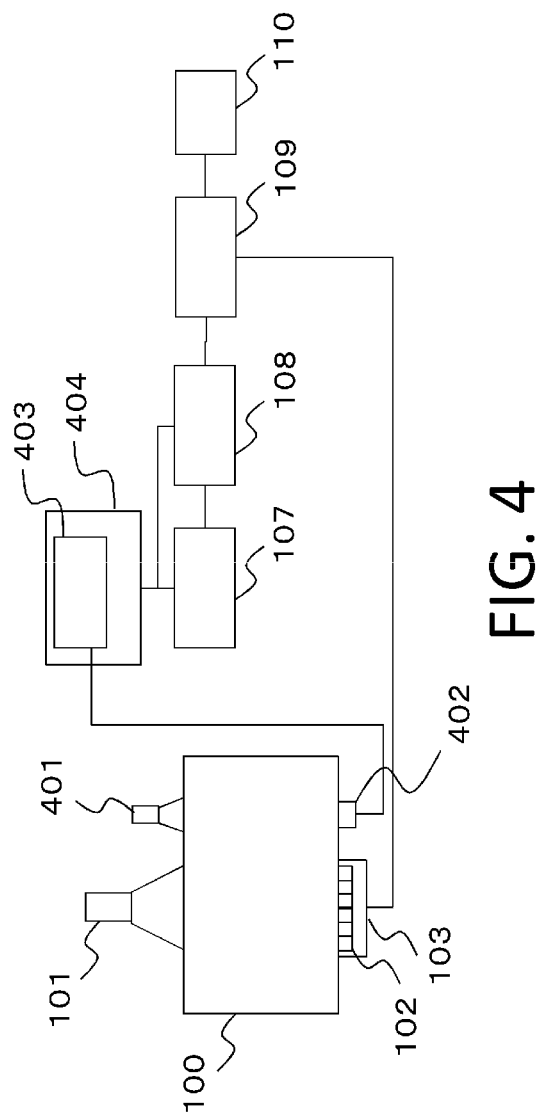
FIG. 4 is a diagram showing an overview of a photoacoustic imaging apparatus in a second embodiment.

FIG. 4 is a diagram showing an overview of a photoacoustic imaging apparatus in a second embodiment of the present invention. In the second embodiment, when compared to the first embodiment, the optical characteristic value input unit is replaced with an optical characteristic value measurement unit 403, and a light source 401 and a light detection unit 402 are added. Since other components are the same as in the first embodiment, description is omitted regarding terms that are the same. Only configurations that differ from the first embodiment will be described below.

The light source 401 that is unit of light irradiation for optical characteristic value measurement irradiates the object 100 with light (optical characteristic value measurement light) for measuring the optical characteristic value (the absorption coefficient that is the absorption characteristic value and the equivalent scattering coefficient that is the scattering characteristic value) of the object 100. It is desirable that the wavelength of radiated light be close to the wavelength of light radiated by the irradiation unit 101. For the light source 401, a light source that generates either pulsed light or intensity-modulated light may be used. For example, a laser diode may be used. In the case of pulsed light, it is desirable that the pulse width be several to several hundreds of picoseconds (ps). In the case of intensity-modulated light, it is desirable that the frequency of intensity modulation be several to several hundreds of megahertz.

The light detection unit 402 that is unit of detecting light for optical characteristic value measurement detects the optical characteristic value measurement light that is radiated by the light source 401 and has propagated inside the object 100. A detector that responds quickly with respect to at least the pulse width or the frequency of intensity modulation is desirable. For example, a photomultiplier, an avalanche photodiode, a photodiode, or the like may be used. A detection light signal obtained through detection of the optical characteristic value measurement light is output to the optical characteristic value measurement unit 403 that is characteristic measuring unit.

The optical characteristic value measurement unit 403 calculates the absorption coefficient and the reduced scattering coefficient of the object 100 using the detection light signal output from the light detection unit 402. For calculation, an analytical solution or numerical solution method of transport equations, an analytical solution or numerical solution method of diffusion approximation equations, a numerical solution method using a Monte Carlo method, or the like may be used.

In the case where the light source 401 generates pulsed light, the absorption coefficient and the reduced scattering coefficient are changed such that an analytical solution and the time waveform of the detection light signal match, and the absorption coefficient and the equivalent scattering coefficient at the time of a sufficient match is assumed as the absorption coefficient and the equivalent scattering coefficient of the object. In a similar manner, a numerical solution of the time waveform using a numerical solution method and the time waveform of the detection light signal may be caused to match.

In the case where the light source 401 generates intensity-modulated light, an analytical solution and the detection light signal are caused to match in the decay rate of intensity modulation amplitude (amplitude decay rate) of the detection light signal with respect to the intensity modulation amplitude at the time of incidence upon the object 100 and the phase delay of the intensity modulation of the detection light signal. The amplitude decay rate and the phase delay using a numerical solution method may also be used.

The absorption coefficient and the equivalent scattering coefficient of the object measured by the optical characteristic value measurement unit 403 in this manner is set in the light intensity distribution calculation unit 107 and the light intensity domain setting unit 108 by the optical characteristic value setting unit 404.

Figure 5:
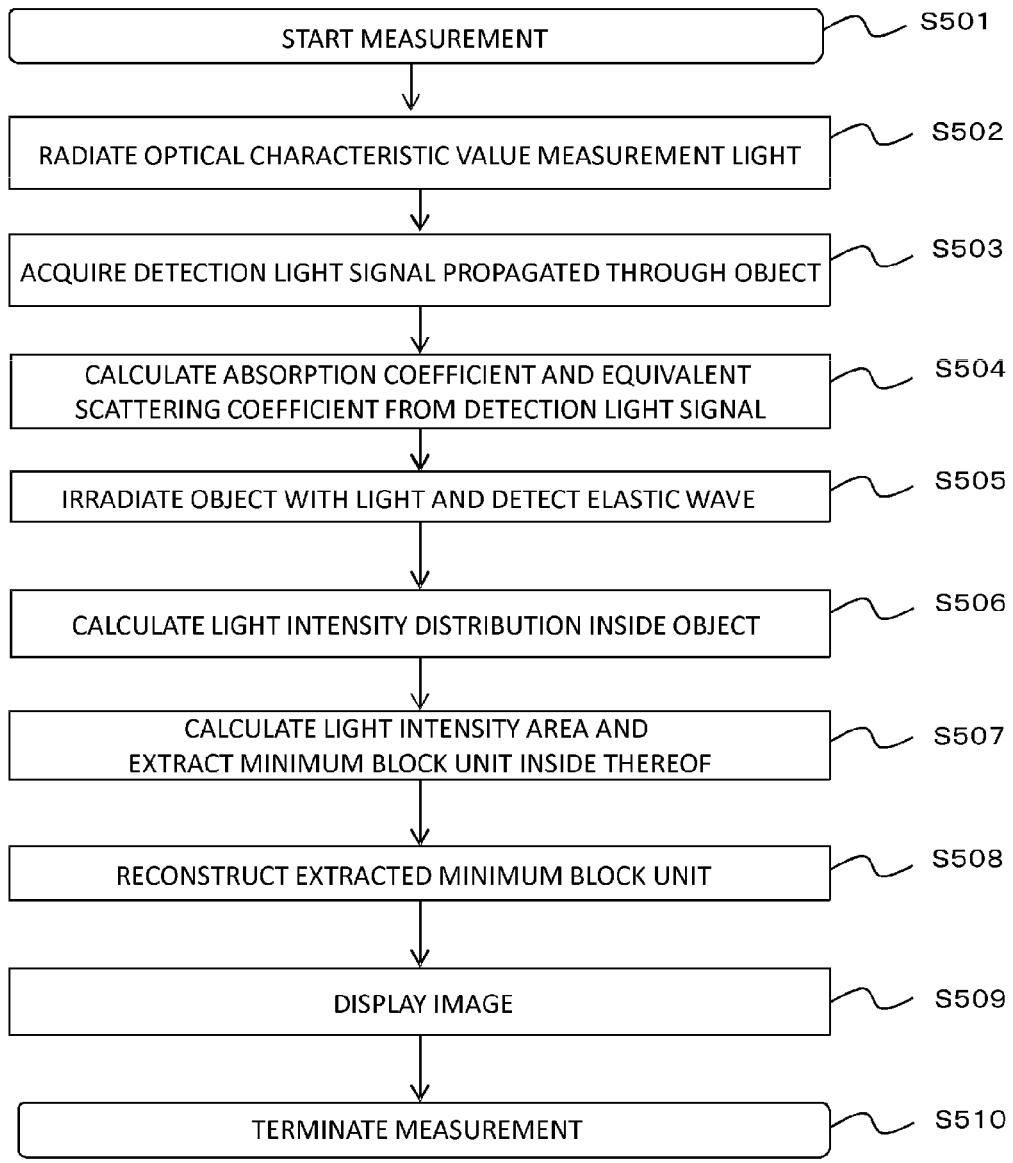
FIG. 5 is a diagram showing the flow of measurement in the second embodiment.

The flow of measurement in the second embodiment is shown in FIG. 5. For FIG. 5, description of steps in which the same processes as in FIG. 3 are performed will be omitted.

Step S501 is the same as step S301 in the first embodiment.

In step S502, the object 100 is irradiated with the optical characteristic value measurement light from an optical characteristic value measurement light irradiation light source 401.

In step S503, the optical characteristic value measurement light having propagated in the object 100 is detected by an optical characteristic value measurement light detector 402 to obtain the detection light signal.

In step S504, the absorption coefficient and the reduced scattering coefficient of the object 100 are calculated in the optical characteristic value measurement unit 403 using the detection light signal obtained in step S503.

Step S505 is the same as step S303 in the first embodiment.

In step S506 that is a distribution acquiring step, the light intensity distribution inside the object 100 is calculated in the light intensity distribution calculation unit 107 using the absorption coefficient and the reduced scattering coefficient obtained through measurement in step S503.

In step S507 that is a setting step, a light intensity domain is calculated and a minimum block unit inside the light intensity domain is extracted by the light intensity domain setting unit 108 using the absorption coefficient obtained through measurement in step S503 and the light intensity distribution obtained in step S506. The extracted minimum block unit is set in the reconstruction unit 109.

Step S508 is the same as step S306 in the first embodiment.

Step S509 is the same as step S307 in the first embodiment.

In step S510, the measurement is terminated.

In the second embodiment, the minimum block units to be reconstructed can be reduced and the time until acquisition of the object information can be shortened by selectively reconstructing the minimum block unit included in a domain having sufficient light intensity obtained from the optical characteristic value of the object obtained through measurement. By using the absorption coefficient and the reduced scattering coefficient of the object obtained through measurement, the domain with sufficient light intensity can be designated with higher precision.

Third Embodiment

In a third embodiment, a domain to be imaged is limited based on the light intensity distribution inside an object prepared in advance. Accordingly, since the time of acquiring the light intensity distribution can be shortened compared to other embodiments, the time required for acquisition of object information can be shortened further.

Figure 6:
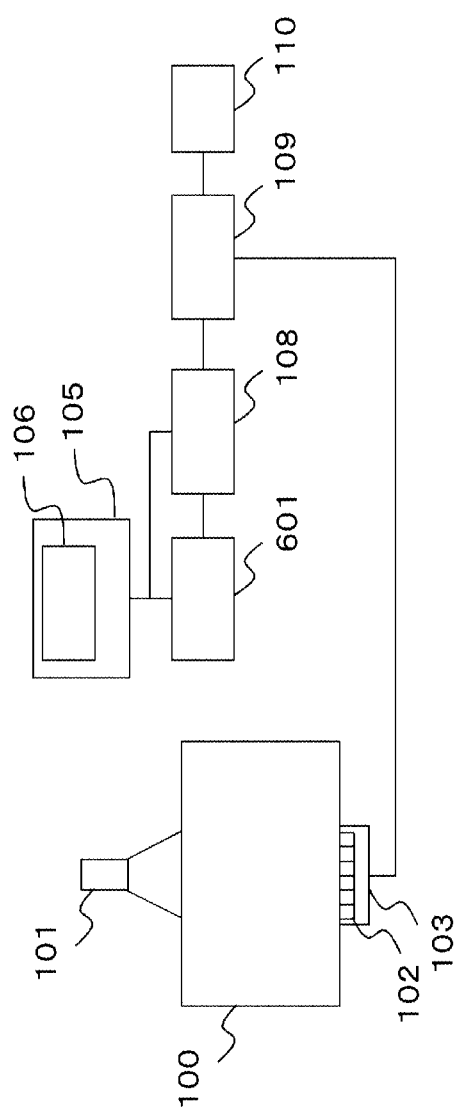
FIG. 6 is a diagram showing an overview of a photoacoustic imaging apparatus in a third embodiment.

FIG. 6 is a diagram showing an overview of a photoacoustic imaging apparatus in the third embodiment of the present invention. In the third embodiment, the light intensity distribution calculation unit 107 is replaced with a light intensity distribution storage unit 601 when compared to the first embodiment. Since other components are the same as in the first embodiment, description is omitted regarding terms that are the same. Only configurations that differ from the first embodiment will be described below.

The light intensity distribution storage unit 601 stores the light intensity distribution calculated in advance. For example, the light intensity distribution can be stored as volume data showing the inside of the object 100. As the light intensity distribution storage unit 601, a hard disk, a non-volatile memory, or the like may be used. The light intensity distribution to be stored can be calculated using a general optical characteristic value for a biological body. In calculating in advance the light intensity distribution to be stored, the intensity distribution pattern of irradiation light measured in advance can be reflected.

Note that the light intensity distribution storage unit 601 preferably can store a plurality of light intensity distributions. That is, a light intensity distribution corresponding to the optical characteristic value of the object set by the optical characteristic value setting unit 105 can be selected. Since there are endless patterns to the optical characteristic value and it is difficult to store all of the corresponding light intensity distributions at this time, it is recommended that light intensity distributions for a limited number of patterns of the optical characteristic value be stored. In the case where a certain optical characteristic value is input, one that is closest to the optical characteristic value among the limited number of optical characteristic values is selected, and a light intensity distribution corresponding to the selected optical characteristic value is used.

Note that a general value for a biological body, a statistical value according to the characteristic of the object 100, a measured value obtained through measurement of the object 100, or the like may be used for the optical characteristic value to be set. Although the light intensity distribution is stored in the light intensity distribution storage unit 601 in this embodiment, the light intensity domain setting unit 108 may be included in the light intensity distribution storage unit 601 to store the light intensity distribution.

Figure 7:
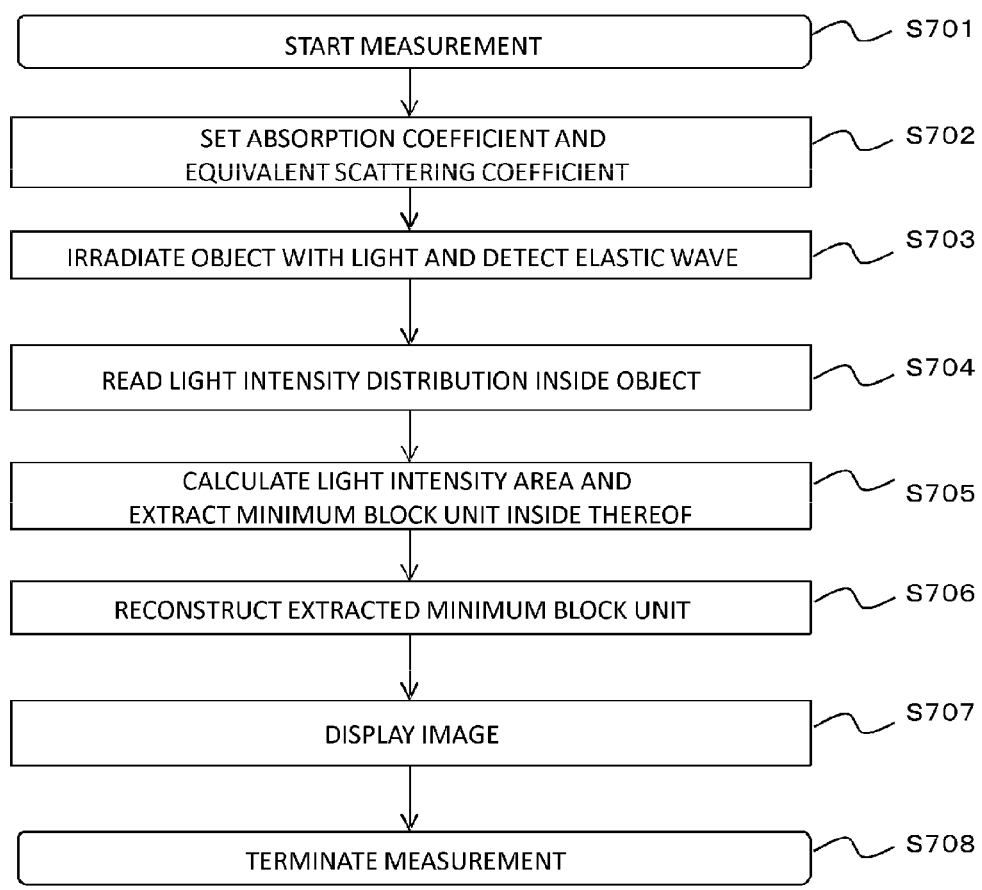
FIG. 7 is a diagram showing the flow of measurement in the third embodiment.

The flow of measurement in this embodiment is shown in FIG. 7. For FIG. 7, description of steps in which the same processes as in FIG. 3 are performed will be omitted.

Step S701 is the same as step S301.

In step S702 that is a characteristic setting step, an operator executes a characteristic inputting step of inputting an optical characteristic value (the absorption coefficient and the reduced scattering coefficient) of the object 100 from the optical characteristic value input unit 105. The input absorption coefficient and equivalent scattering coefficient are set in the light intensity distribution storage unit 601 and the light intensity domain setting unit 108. Alternatively, the optical characteristic value obtained through measurement of the object 100 is set in the light intensity distribution storage unit 601 and the light intensity distribution calculation unit 107.

In step S704 that is a distribution acquiring step, the light intensity distribution corresponding to the optical characteristic value set in step S703 is read from the light intensity distribution storage unit 601 to obtain the light intensity distribution inside the object 100. Alternatively, the light intensity domain is read in the case where the light intensity domain is stored in the light intensity distribution storage unit 601. In this case, calculation of the light intensity domain in step S705 is omitted.

Steps S705 to S708 are respectively the same as steps S305 to S308.

In the third embodiment, a minimum block unit included in a domain having sufficient light intensity acquired from the light intensity distribution calculated in advance is selectively reconstructed. Accordingly, since the number of minimum block units to be reconstructed can be reduced and the time required for acquisition of the light intensity distribution can be shortened, the time until acquisition of the object information can be shortened further.

Fourth Embodiment

In a fourth embodiment, the number of minimum block units to be reconstructed can be reduced and the time until acquisition of object information can be shortened compared to other embodiments by selectively reconstructing the minimum block unit included in both a domain of the directivity range of a transducer and a domain having sufficient light intensity.

(Apparatus Configuration)

Figure 8:
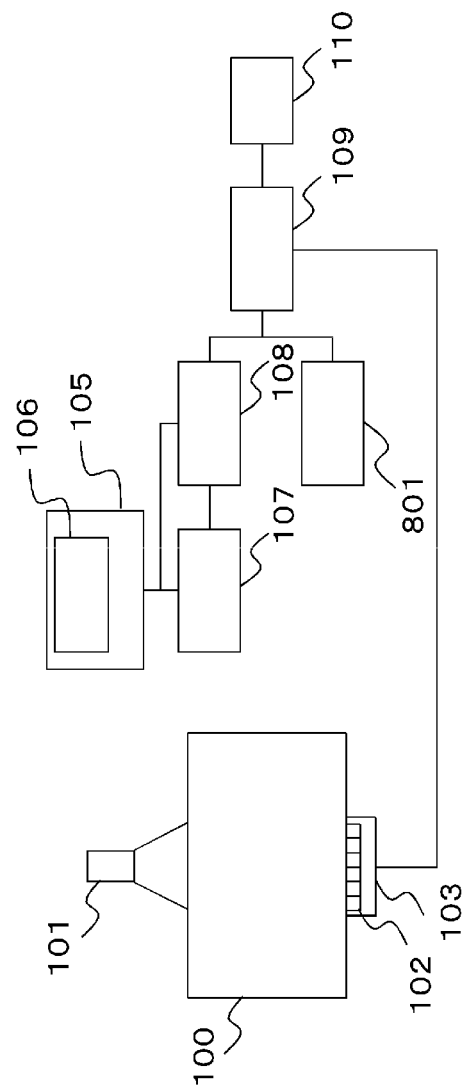
FIG. 8 is a diagram showing an overview of a photoacoustic imaging apparatus in a fourth embodiment.

FIG. 8 is a diagram showing an overview of a photoacoustic imaging apparatus in the fourth embodiment of the present invention. In the fourth embodiment, a directivity range domain setting unit 801 is added and the behavior of the reconstruction unit 109 differs when compared to the first embodiment. Since other components are the same as in the first embodiment, description is omitted regarding terms that are the same. Only configurations that differ from the first embodiment will be described below.

With the directivity range domain setting unit 801 that is directivity setting unit, the minimum block unit within the directivity range of the transducer 102 among the minimum block units forming the object 100 is extracted and set in the reconstruction unit 109. A directivity range is a domain determined by a directivity angle that is the angle in which the transducer 102 can receive an elastic wave. The directivity range will be described using FIG. 9.

Figure 9:
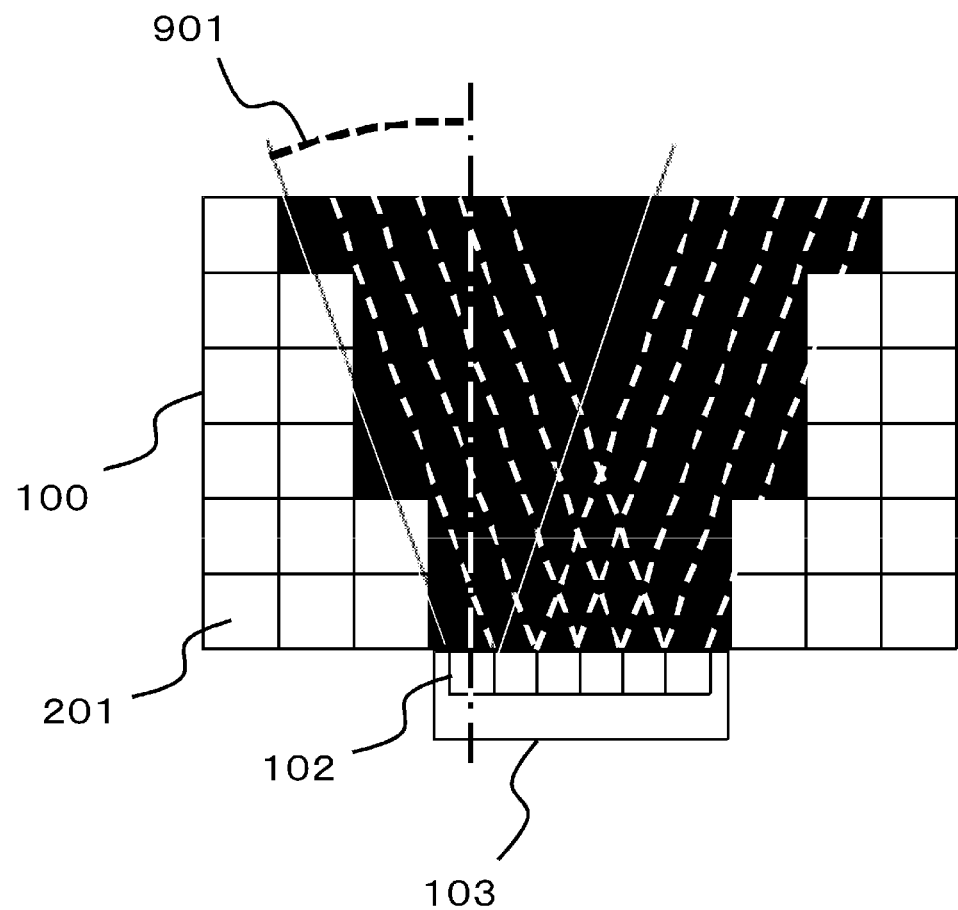
FIG. 9 is a diagram showing the directivity range in the fourth embodiment.

In FIG. 9, reference numeral 901 denotes the directivity angle of one transducer 102. Herein, a case where the directivity angle is 20° is shown. An elastic wave generated in a range inside the directivity angle 901 can be detected by the transducer 102. Thus, an elastic wave generated in a range inside the directivity angle of any one of the plurality of transducers 102 forming the probe 103 can be output from the probe 103 as a received signal. That is, a portion shown in black in FIG. 2 among the minimum block units 201 can be reconstructed from the received signal. The domain shown in black is the directivity range. Note that the directivity angle can be specified in various ways according to the precision desired in the measurement or the characteristic of the transducer. For example, in the case where the receiving sensitivity is maximum in the normal direction of the transducer, the directivity angle may be a range of a half width that enables reception with intensity half the maximum sensitivity.

Figure 10:
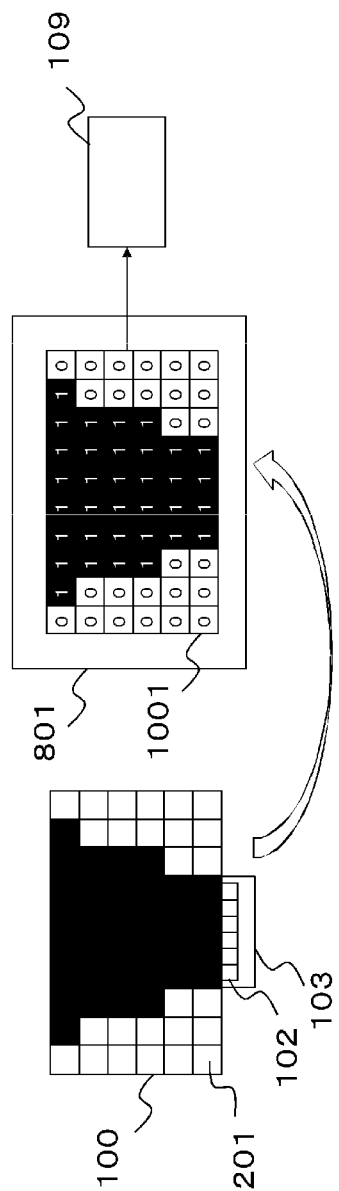
FIG. 10 is a diagram showing the details of a directivity range domain setting unit in the fourth embodiment.

As shown in FIG. 10, the directivity range domain setting unit 801 includes a directivity range storage unit 1001 that stores a value corresponding to each minimum block unit forming the object 100. In the directivity range storage unit 1001, a storage area corresponding to the minimum block units within the directivity range is set to 1, and a storage area corresponding to other minimum block units is set to 0. The directivity range domain setting unit 801 sets, in the reconstruction unit 109, the minimum block unit that is present inside the directivity range by outputting a value of the directivity range storage unit 1001 to the reconstruction unit 109.

The reconstruction unit 109 selectively reconstructs the minimum block unit set in both the light intensity domain setting unit 108 that is setting unit and the directivity range domain setting unit 801 that is the directivity setting unit among the minimum block units forming the object 100. The details will be described below.

Figure 11:
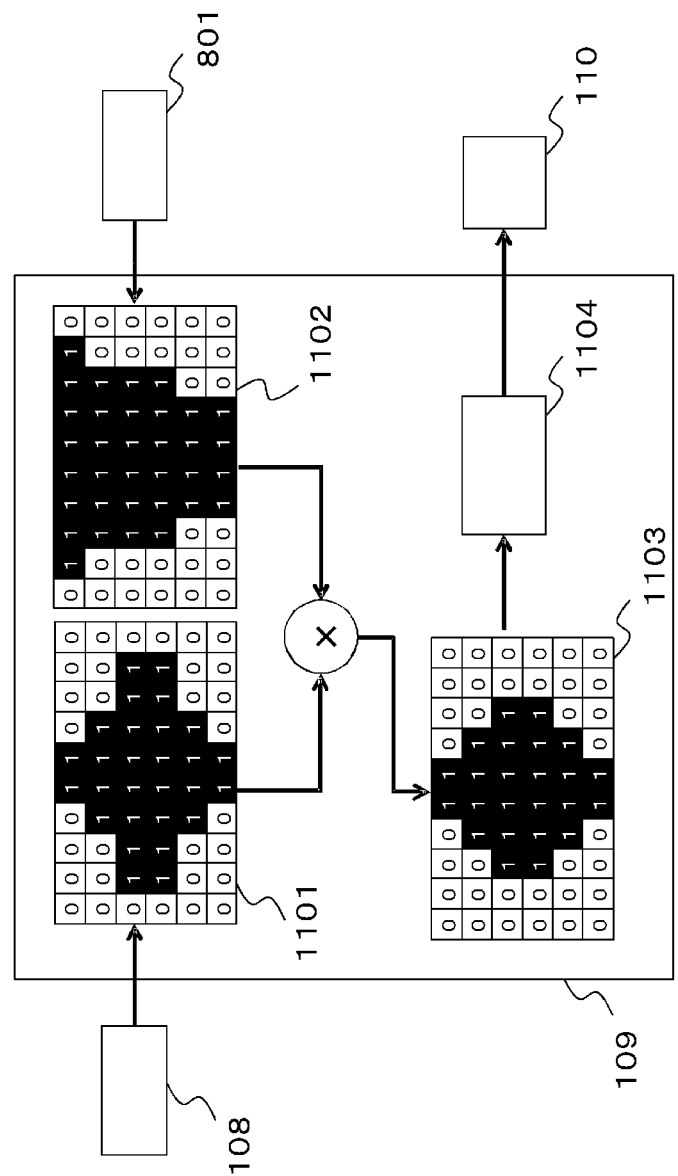
FIG. 11 is a diagram showing the details of a reconstruction unit in the fourth embodiment.

FIG. 11 is a diagram showing the details of the reconstruction unit 109. Reference numeral 1101 denotes data showing the minimum block unit within the light intensity domain set by the light intensity distribution calculation unit 107, and reference numeral 1102 denotes data showing the minimum block unit within the directivity range domain set by the directivity range domain setting unit 801. The reconstruction unit 109 performs a multiplication operation for each minimum block unit corresponding to reference numeral 1101 and reference numeral 1102. The result of the multiplication operation is stored in a storage area of the corresponding minimum block unit in a reconstruction domain storage unit 1103. A reconstruction processing unit 1104 performs reconstruction of the minimum block unit that is set to 1 by the reconstruction domain storage unit and generates data with which the inside of the object is imaged.

Figure 12:
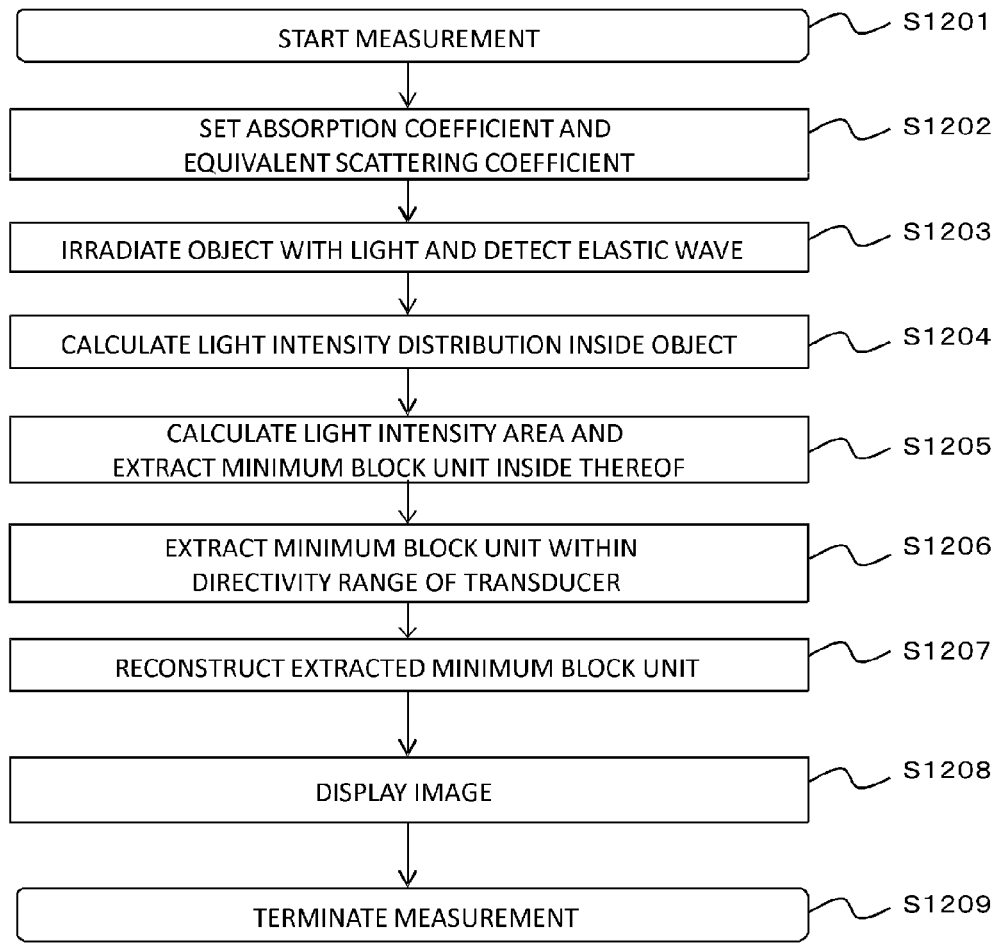
FIG. 12 is a diagram showing the flow of measurement in the fourth embodiment.

The flow of measurement in this embodiment is shown in FIG. 12. For FIG. 12, description of steps in which the same processes as in FIG. 3 are performed will be omitted.

Step S1201 to step S1205 are respectively the same as step S301 to step S305.

In step S1206 that is a directivity setting step, the minimum block unit included in the domain within the directivity range of the transducer 102 is extracted. The extracted minimum block unit is set in the reconstruction unit 109.

In step S1207 that is a generating step, the minimum block unit extracted and set in both step S1205 and step S1206 is reconstructed in the reconstruction unit 109 using the received signal obtained in step S1203. Accordingly, image data of the inside of the object is obtained.

Step S1208 and step S1209 are respectively the same as step S307 and step S308.

In the fourth embodiment above, the number of minimum block units to be reconstructed can be reduced and the time until acquisition of the object information can be shortened compared to other embodiments by selectively reconstructing the minimum block unit included in both the domain of the directivity range of the transducer and the domain having sufficient light intensity.

Note that the minimum block unit included in the domain of the directivity range of the transducer may be selectively reconstructed. That is, the minimum block unit not included in the domain of the range of the directivity of the transducer may be not reconstructed. Accordingly, the time until acquisition of the object information can be shortened.

With the present invention, as described above, a domain within an object to be reconstructed is set in consideration of the light intensity distribution within the object in photoacoustic imaging. Since a domain with light intensity that generates an elastic wave of sufficient sound pressure is selected and reconstructed as a result, the time until acquisition of object information can be shortened.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-251317, filed on Nov. 15, 2012, which is hereby incorporated by reference herein in its entirety.

What is claimed is:

1. An object information acquisition apparatus comprising:
   an irradiating unit configured to irradiate an object with light;
   a detecting unit configured to output a signal by receiving an elastic wave generated from the object irradiated with light;
   a distribution acquiring unit configured to acquire a light intensity distribution within the object irradiated with light;
   a setting unit configured to select a minimum block unit in which light intensity is lower than a predetermined threshold value, using the light intensity distribution; and
   a generating unit configured to acquire object information using the outputted signal,
   wherein acquisition of object information is excluded for the selected minimum block unit.

2. The object information acquisition apparatus according to claim 1, wherein the distribution acquiring unit is configured to acquire the light intensity distribution using an optical characteristic value.

3. The object information acquisition apparatus according to claim 2, wherein the optical characteristic value includes an absorption characteristic value of the object and a scattering characteristic value.

4. The object information acquisition apparatus according to claim 3, wherein the setting unit is configured to set the predetermined threshold value by dividing a noise equivalent sound pressure of the outputted signal by the absorption characteristic value and a Gruneisen coefficient of the object.

5. The object information acquisition apparatus according to claim 3, wherein the setting unit is configured to set the predetermined threshold value such that an elastic wave generated from a minimum block unit of which the absorption characteristic value is greater than an average value of the object can be detected.

6. The object information acquisition apparatus according to claim 2, further comprising a characteristic input unit configured to input the optical characteristic value.

7. The object information acquisition apparatus according to claim 6, wherein the characteristic input unit is configured to accept an input of the optical characteristic value performed by an operator.

8. The object information acquisition apparatus according to claim 2, further comprising a characteristic measuring unit configured to measure the optical characteristic value.

9. The object information acquisition apparatus according to claim 8, wherein the characteristic measuring unit includes a unit configured to irradiate the object with optical characteristic value measurement light for measuring the optical characteristic value, and a unit configured to detect light resulting from the optical characteristic value measurement light having propagated through the object.

10. The object information acquisition apparatus according to claim 1, wherein the setting unit is configured to set the predetermined threshold value based on a noise equivalent sound pressure and an amount of an acoustic decay between an acoustic source arranged at the minimum block unit and the detecting unit.

11. The object information acquisition apparatus according to claim 1, further comprising a distribution storage unit configured to store a light intensity distribution, wherein the distribution acquiring unit is configured to acquire the light intensity distribution by reading out from the distribution storage unit.

12. The object information acquisition apparatus according to claim 11, wherein the distribution acquiring unit is configured to acquire the light intensity distribution by selecting a light intensity distribution corresponding to an optical characteristic value of the subject from a plurality of the light intensity distributions stored in the distribution storage unit.

13. The object information acquisition apparatus according to claim 1,
wherein the setting unit is configured to select a second selected minimum block unit which is not included in a directivity range domain based on a directivity angle of the detecting unit,
wherein acquisition of object information is excluded for both the selected minimum block unit and the second selected minimum block unit.

14. The object information acquisition apparatus according to claim 13,
wherein the setting unit is configured to select a fourth selected minimum block unit in which light intensity is greater than or equal to the predetermined threshold value and which is included in the directivity range domain, and
wherein the generating unit is configured to acquire the object information of the fourth selected minimum block unit.

15. The object information acquisition apparatus according to claim 14,
wherein the setting unit is configured to select a third selected minimum block unit in which light intensity is greater than or equal to the predetermined threshold value, and
wherein the generating unit is configured to acquire the object information of a third selected minimum block unit.

16. The object information acquisition apparatus according to claim 1,
wherein the setting unit is configured to select a third selected minimum block unit in which light intensity is greater than or equal to the predetermined threshold value,
wherein the generating unit is configured to acquire the object information of the third selected minimum block unit.

17. An object information acquisition method comprising:
acquiring a light intensity distribution within an object irradiated with light;
selecting a minimum block unit in which light intensity is lower than a predetermined threshold value, using the light intensity distribution; and
acquiring object information using a signal, the signal being outputted from a detection unit by receiving elastic wave generated from the object irradiated with light,
wherein, in said acquiring of object information, acquisition of object information is excluded for the selected minimum block unit.

18. The object information acquisition method according to claim 17, further comprising:
setting a directivity range domain based on a directivity angle of the detecting unit, and
selecting a second selected minimum block unit which is not included in the directivity range domain,
wherein, in said acquiring of object information, acquisition of object information is excluded for both the selected minimum block unit and the second selected minimum block unit.

19. The object information acquisition method according to claim 18, further comprising:
selecting a fourth selected minimum block unit in which light intensity is greater than or equal to the predetermined threshold value and which is included in the directivity range domain,
wherein, in said acquiring of object information, the object information of the fourth selected minimum block unit is acquired.

20. The object information acquisition method according to claim 17, further comprising:
selecting a third selected minimum block unit in which light intensity is greater than or equal to the predetermined threshold value,
wherein, in said acquiring of object information, the object information of the third selected minimum block unit is acquired.

* * * * *